United States Patent
Baek et al.

(10) Patent No.: US 12,313,974 B2
(45) Date of Patent: May 27, 2025

(54) RESIST UNDERLAYER COMPOSITION, AND METHOD OF FORMING PATTERNS USING THE COMPOSITION

(71) Applicant: Samsung SDI Co., Ltd., Yongin-si (KR)

(72) Inventors: Jaeyeol Baek, Suwon-si (KR); Soonhyung Kwon, Suwon-si (KR); Minsoo Kim, Suwon-si (KR); Hyeon Park, Suwon-si (KR); Shinhyo Bae, Suwon-si (KR); Daeseok Song, Suwon-si (KR); Yoojeong Choi, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 79 days.

(21) Appl. No.: 18/311,627

(22) Filed: May 3, 2023

(65) Prior Publication Data
US 2023/0273523 A1  Aug. 31, 2023

Related U.S. Application Data

(62) Division of application No. 17/153,095, filed on Jan. 20, 2021, now Pat. No. 11,675,271.

(30) Foreign Application Priority Data

Jan. 31, 2020 (KR) .......... 10-2020-0011629

(51) Int. Cl.
*G03F 7/11* (2006.01)
*C07D 251/32* (2006.01)
(Continued)

(52) U.S. Cl.
CPC .............. *G03F 7/11* (2013.01); *C07D 251/32* (2013.01); *G03F 7/0045* (2013.01); *G03F 7/168* (2013.01); *G03F 7/26* (2013.01)

(58) Field of Classification Search
CPC .......... G03F 7/11; G03F 7/0045; G03F 7/168; G03F 7/26; G03F 7/091; G03F 7/094;
(Continued)

(56) References Cited

U.S. PATENT DOCUMENTS

| 3,770,731 A | 11/1973 | Jaeger |
| 2012/0037400 A1* | 2/2012 | Fields ............... C08F 220/24 |
| | | 174/126.1 |

(Continued)

FOREIGN PATENT DOCUMENTS

| CN | 106432686 A | 2/2017 |
| CN | 106980234 A | 7/2017 |

(Continued)

OTHER PUBLICATIONS

Japanese Office Action dated Feb. 1, 2022, of corresponding Japanese Patent Application No. 2021-008711 (2 pages).

(Continued)

*Primary Examiner* — Mark F. Huff
*Assistant Examiner* — Moriah S. Smoot
(74) *Attorney, Agent, or Firm* — Womble Bond Dickinson (US) LLP

(57) ABSTRACT

A resist underlayer composition includes a polymer including a structural unit represented by Chemical Formula 1, and a solvent. A method of forming patterns uses the resist underlayer composition under a photoresist pattern to enhance the sensitivity of the photoresist to an exposure light source, thereby providing enhanced resolution and faster processing times.

(Continued)

Chemical Formula 1

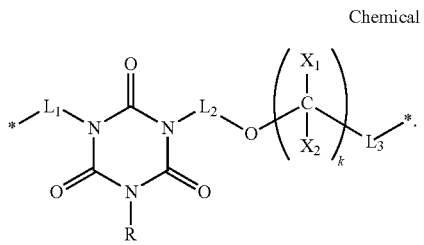

8 Claims, 2 Drawing Sheets (51) Int. Cl.
  *G03F 7/004* (2006.01)
  *G03F 7/16* (2006.01)
  *G03F 7/26* (2006.01)
(58) Field of Classification Search
  CPC .......... G03F 7/004; G03F 7/09; G03F 7/2012;
  G03F 7/2043; C07D 251/32; C07D
  251/30; C08L 67/00; C08L 71/00; C08L
  101/025
  See application file for complete search history.

(56) References Cited

U.S. PATENT DOCUMENTS

| 2014/0170567 | A1 | 6/2014 | Sakamoto et al. |
| 2017/0283651 | A1* | 10/2017 | Sim ............................ G03F 7/11 |
| 2019/0377262 | A1 | 12/2019 | Bae et al. |

FOREIGN PATENT DOCUMENTS

| CN | 107267039 A | 10/2017 |
| CN | 110579943 A | 12/2019 |
| EP | 3 498 756 A1 | 6/2019 |
| JP | 2009-093162 A | 4/2009 |
| JP | 2013-033276 A | 2/2013 |
| JP | 6083537 B2 | 2/2017 |
| JP | 2017-187764 A | 10/2017 |
| JP | 2019-70132 A | 5/2019 |
| KR | 10-2014-0018556 A | 2/2014 |
| KR | 10-2014-0050046 A | 4/2014 |
| KR | 10-2017-0114257 A | 10/2017 |
| KR | 10-2019-0049171 A | 5/2019 |
| KR | 10-2019-0057336 A | 5/2019 |
| KR | 10-2019-0140261 A | 12/2019 |
| TW | 201805379 A | 2/2018 |
| WO | WO 2007/148627 A1 | 12/2007 |
| WO | WO 2009/075265 A1 | 6/2009 |
| WO | WO 2010/061774 A1 | 6/2010 |
| WO | WO 2013/141015 A1 | 9/2013 |
| WO | WO 2018/056410 A1 | 3/2018 |

OTHER PUBLICATIONS

Taiwanese Office Action (including search report) dated Mar. 25, 2022, of corresponding Taiwanese Patent Application No. 110102956 (5 pages).
Chinese Office Action (including a search report) dated Mar. 27, 2024 of the corresponding Chinese Patent Application No. 202110115902.X (7 pages).

* cited by examiner

RESIST UNDERLAYER COMPOSITION, AND METHOD OF FORMING PATTERNS USING THE COMPOSITION

CROSS-REFERENCE TO RELATED APPLICATION

This application is a divisional of U.S. patent application Ser. No. 17/153,095, filed Jan. 20, 2021, which claims priority to and the benefit of Korean Patent Application No. 10-2020-0011629, filed in the Korean Intellectual Property Office on Jan. 31, 2020, the entire content of all of which are incorporated herein by reference.

BACKGROUND

1. Field

One or more aspects of embodiments of the present disclosure relate to a resist underlayer composition, and a method of forming patterns using the same.

2. Description of the Related Art

Recently, the semiconductor industry has developed to an ultrafine technique (e.g., level of technology) having a pattern size on a scale of several to several tens of nanometers. Effective lithographic techniques are desired for production of such ultrafine semiconductor devices.

The quality of the exposure performed during formation of the photoresist pattern is among the important factors for obtaining a photoresist image with a high resolution.

The exposure of a photoresist is performed utilizing activated radiation, which is often reflected and thus restricts or reduces the resolution of an image patterned in the photoresist layer. For example, when the radiation is reflected from the interface between the substrate and the photoresist layer or on an interlayer hard mask, and is scattered into a photoresist region, the photoresist linewidth may become non-uniform and pattern formality may be obstructed or decreased.

A photoresist underlayer composition may desirably absorb the reflected radiation and may simultaneously have a high etch selectivity with respect to the photoresist, for example by having chemical resistance against a solvent utilized a subsequent process after thermal curing, and excellent adherence to the photoresist to help with patterning the photoresist.

In order to decrease the reflected radiation, an organic "resist underlayer" between a substrate and a photoresist layer has been used in attempts to absorb light passing through the photoresist and simultaneously improve etch selectivity, chemical resistance, and adherence to the photoresist.

As the resolution of a semiconductor pattern is increased, the wavelength of activated radiation used to expose photoresist is shortened, and for example, may be sourced from an i-line (wavelength of 365 nm), a KrF excimer laser (wavelength of 248 nm), an ArF excimer laser (wavelength of 193 nm), and/or the like, and accordingly, a resist underlayer capable of forming an ultrafine pattern of about 10 nm by using an EUV (extreme ultraviolet) light source in a patterning process is desired.

SUMMARY

One or more aspects of embodiments of the present disclosure are directed toward a resist underlayer composition capable of exhibiting improved light absorption efficiency for EUV, thereby improving the sensitivity of a photoresist.

One or more aspects of embodiments of the present disclosure are directed toward a method of forming patterns using the resist underlayer composition.

One or more embodiments of the present disclosure provide a resist underlayer composition including a polymer including a structural unit represented by Chemical Formula 1, and a solvent:

Chemical Formula 1

In Chemical Formula 1,
$L_1$, $L_2$, and $L_3$ may each independently be a substituted or unsubstituted C1 to C10 alkylene group, a substituted or unsubstituted C1 to C10 heteroalkylene group, a substituted or unsubstituted C3 to C20 cycloalkylene group, a substituted or unsubstituted C2 to C20 heterocycloalkylene group, a substituted or unsubstituted C6 to C20 arylene group, a substituted or unsubstituted C1 to C10 heteroarylene group, a carbonyl group, an ester group, or a combination thereof, R may be hydrogen, deuterium, a halogen (—F, —Cl, —Br, or —I), a substituted or unsubstituted C1 to C10 alkyl group, a substituted or unsubstituted C2 to C20 alkenyl group, a substituted or unsubstituted C2 to C20 alkynyl group, a substituted or unsubstituted C3 to C20 cycloalkyl group, a substituted or unsubstituted C6 to C20 aryl group, a substituted or unsubstituted C1 to C10 heteroalkyl group, a substituted or unsubstituted C2 to C20 heteroalkenyl group, a substituted or unsubstituted C3 to C20 heterocycloalkyl group, or a substituted or unsubstituted C6 to C20 heteroaryl group, $X_1$ and $X_2$ may each independently be a halogen (—F, —Cl, —Br, or —I), a substituted or unsubstituted C1 to C10 alkyl group, a substituted or unsubstituted C1 to C10 heteroalkyl group, a substituted or unsubstituted C3 to C20 cycloalkyl group, a substituted or unsubstituted C3 to C20 heterocycloalkyl group, a substituted or unsubstituted C6 to C20 aryl group, or a substituted or unsubstituted C6 to C20 heteroaryl group, provided that at least one of $X_1$ or $X_2$ is selected from a halogen (—F, —Cl, —Br, or —I), and k may be an integer of 1 to 10, and * is a linking point.

One or more embodiments of the present disclosure provide a method of forming patterns, the method including: forming an etching target layer on a substrate, coating the resist underlayer composition according to an embodiment on the etching target layer to form a resist underlayer, forming a photoresist pattern on the resist underlayer, and sequentially etching the resist underlayer and the etching target layer using the photoresist pattern as an etching mask.

The resist underlayer composition according to an embodiment may exhibit improved light absorption efficiency for EUV, thereby improving the sensitivity of a photoresist.

DETAILED DESCRIPTION

Embodiments of the present disclosure will hereinafter be described in more detail, and may be easily performed by a person skilled in the art. However, this disclosure may be embodied in many different forms and is not construed as limited to the example embodiments set forth herein.

In the drawings, the thickness of layers, films, panels, regions, etc., may be exaggerated for clarity, and like reference numerals designate like elements throughout the specification and duplicative descriptions thereof may not be provided. It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

As used herein, expressions such as "at least one of," "one of," and "selected from," when preceding a list of elements, modify the entire list of elements and do not modify the individual elements of the list. As used herein, the term "and/or" includes any and all combinations of one or more of the associated listed items.

Further, the use of "may" when describing embodiments of the present disclosure refers to "one or more embodiments of the present disclosure". The expression "at least one of a, b or c" may indicate only a, only b, only c, both a and b, both a and c, both b and c, all of a, b, and c, or variations thereof. Also, the expression "at least one selected from a, b and c" may indicate only a, only b, only c, both a and b, both a and c, both b and c, all of a, b, and c, or variations thereof.

As used herein, when a definition is not otherwise provided, the term "substituted" refers to replacement of at least one hydrogen atom of a compound or group with a substituent selected from a halogen group (—F, —Br, —Cl, or —I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a vinyl group, a C1 to C20 alkyl group, a C2 to C20 alkenyl group, a C2 to C20 alkynyl group, a C6 to C30 aryl group, a C7 to C30 arylalkyl group, a C6 to C30 allyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, the term "hetero" refers to the inclusion of one or more (e.g., 1 to 3 heteroatoms) selected from N, O, S, and P.

Unless otherwise specified in the present specification, the weight average molecular weight is measured by dissolving a powder sample in tetrahydrofuran (THF) and analyzing the resulting solution using a 1200 series Gel Permeation Chromatography (GPC) by Agilent Technologies (equipped with a column by Shodex Company LF-804, standard sample is Shodex company polystyrene).

Hereinafter, a resist underlayer composition according to an embodiment is described.

A resist underlayer composition according to an embodiment includes a polymer including a structural unit represented by Chemical Formula 1, and a solvent.

Chemical Formula 1

In Chemical Formula 1, $L_1$, $L_2$, and $L_3$ may each independently be a substituted or unsubstituted C1 to C10 alkylene group, a substituted or unsubstituted C1 to C10 heteroalkylene group, a substituted or unsubstituted C3 to C20 cycloalkylene group, a substituted or unsubstituted C2 to C20 heterocycloalkylene group, a substituted or unsubstituted C6 to C20 arylene group, a substituted or unsubstituted C1 to C10 heteroarylene group, a carbonyl group, an ester group, or a combination thereof, R may be hydrogen, deuterium, a halogen (—F, —Cl, —Br, or —I), a substituted or unsubstituted C1 to C10 alkyl group, a substituted or unsubstituted C2 to C20 alkenyl group, a substituted or unsubstituted C2 to C20 alkynyl group, a substituted or unsubstituted C3 to C20 cycloalkyl group, a substituted or unsubstituted C6 to C20 aryl group, a substituted or unsubstituted C1 to C10 heteroalkyl group, a substituted or unsubstituted C2 to C20 heteroalkenyl group, a substituted or unsubstituted C3 to C20 heterocycloalkyl group, or a substituted or unsubstituted C6 to C20 heteroaryl group, $X_1$ and $X_2$ may each independently be a halogen (—F, —Cl, —Br, or —I), a substituted or unsubstituted C1 to C10 alkyl group, a substituted or unsubstituted C1 to C10 heteroalkyl group, a substituted or unsubstituted C3 to C20 cycloalkyl group, a substituted or unsubstituted C3 to C20 heterocycloalkyl group, a substituted or unsubstituted C6 to C20 aryl group, or a substituted or unsubstituted C6 to C20 heteroaryl group, provided that at least one of $X_1$ or $X_2$ is a halogen (—F, —Cl, —Br, or —I), k may be an integer of 1 to 10, and

* is a linking point where two or more structural units are linked to each other.

In an embodiment, each of $L_1$, $L_2$, and $L_3$ may be the same as or different from each other.

In an embodiment, $L_1$, $L_2$, and $L_3$ may each independently be a substituted or unsubstituted C1 to C10 alkylene group, a substituted or unsubstituted C1 to C10 heteroalkylene group, a substituted or unsubstituted C3 to C20 cycloalkylene group, a substituted or unsubstituted C2 to C20 heterocycloalkylene group, a carbonyl group, an ester group, or a combination thereof.

In an embodiment, at least one of $L_1$, $L_2$, or $L_3$ may be a substituted or unsubstituted C1 to C10 alkylene group, a substituted or unsubstituted C1 to C10 heteroalkylene group, a carbonyl group, or a combination thereof. For example, at least one of $L_1$, $L_2$, or $L_3$ may each independently be a substituted or unsubstituted C1 to C10 heteroalkylene group, a substituted or unsubstituted C1 to C10 alkylene group with a carbonyl group, or a substituted or unsubstituted C1 to C10 heteroalkylene group with a carbonyl group.

In an embodiment, at least one of $L_1$, $L_2$, or $L_3$ may each independently be a halogen-substituted C1 to C10 heteroalkylene group, or a halogen-substituted C1 to C10 alkylene group.

In an embodiment, each of $X_1$ and $X_2$ may be the same as or different from each other. When $X_1$ and $X_2$ are the same, $X_1$ and $X_2$ may each be the same functional group, and for example may be the same halogen group (e.g., —F).

In an embodiment, one of $X_1$ and $X_2$ may be a halogen, and the other may be a halogen-substituted C1 to C10 alkyl group, a halogen-substituted C1 to C10 heteroalkyl group, a halogen-substituted C3 to C20 cycloalkyl group, or a halogen-substituted C3 to C20 heterocycloalkyl group. For example, when $X_1$ is a halogen group, $X_2$ may be a halogen-substituted C1 to C10 alkyl group, or a halogen-substituted C1 to C10 heteroalkyl group. In the halogen-substituted C1 to C10 alkyl group and the halogen-substituted C1 to C10 heteroalkyl group, at least one of the hydrogen atoms linked to the terminal portion (e.g., at the terminal end) of the group may be substituted with a halogen atom.

For example, the structural unit represented by Chemical Formula 1 may be or include a structural unit represented by Chemical Formula 2:

Chemical Formula 2

In Chemical Formula 2, $L_{11}$ and $L_{13}$ may each independently be a substituted or unsubstituted C1 to C10 alkylene group, a substituted or unsubstituted C1 to C10 heteroalkylene group, a substituted or unsubstituted C3 to C20 cycloalkylene group, a substituted or unsubstituted C2 to C20 heterocycloalkylene group, a carbonyl group, an ester group, or a combination thereof, $L_{12}$ may be a substituted or unsubstituted C1 to C10 alkylene group, a substituted or unsubstituted C1 to C10 heteroalkylene group, a substituted or unsubstituted C3 to C20 cycloalkylene group, or a substituted or unsubstituted C2 to C20 heterocycloalkylene group, $R_1$ may be hydrogen, deuterium, a halogen (—F, —Cl, —Br, —I), a substituted or unsubstituted C1 to C10 alkyl group, a substituted or unsubstituted C3 to C20 cycloalkyl group, a substituted or unsubstituted C6 to C20 aryl group, a substituted or unsubstituted C1 to C10 heteroalkyl group, a substituted or unsubstituted C3 to C20 heterocycloalkyl group, or a substituted or unsubstituted C6 to C20 heteroaryl group,

$X_{11}$ and $X_{12}$ may each independently be a halogen (—F, —Cl, —Br, or —I), a substituted or unsubstituted C1 to C10 alkyl group, a substituted or unsubstituted C1 to C10 heteroalkyl group, a substituted or unsubstituted C3 to C20 cycloalkyl group, or a substituted or unsubstituted C3 to C20 heterocycloalkyl group, provided that at least one of $X_{11}$ or $X_{12}$ is a halogen (—F, —Cl, —Br, —I), k1 may be an integer of 1 to 10, n may be an integer of 2 to 100, and

* is a linking point.

In some embodiments, the polymer including the structural unit may be or include one or more structural units represented by Chemical Formulae 3 to 6.

Chemical Formula 3

Chemical Formula 4

Chemical Formula 5

-continued

Chemical Formula 6

In Chemical Formulae 3 to 6, * is a linking point.

For example, when the polymer constituting the resist underlayer composition includes an isocyanurate-based compound (e.g., monomer or structural unit) having a halogen introduced into the side chain (e.g., a halogenated side chain), for example, an isocyanurate-based compound having a chemical bond in the form of "—O—CH$_2$—C(-halogen)-" in the main chain and/or side chain, the isocyanurate-based compound may improve light absorption efficiency of an exposure light source during exposure of the resist underlayer composition.

Accordingly, when the resist underlayer composition is utilized to form a resist underlayer, secondary electrons may be additionally generated during the photo process. The additionally-generated secondary electrons may affect the photoresist during the photo process, for example by maximizing or increasing acid generation efficiency, and may accordingly improve a photo processing rate of the photoresist and/or enhance sensitivity of the photoresist.

In addition, the polymer including the isocyanurate-based compound may have excellent or suitable solubility in organic solvents (such as propylene glycol methyl ether (PGME) and/or the like), even if polymerized in a relatively high molecular weight state. Accordingly, the resist underlayer composition may exhibit excellent or suitable coating properties and/or stripping resistance due to the excellent or suitable solubility in the organic solvents.

Furthermore, because the polymer is stable against organic solvents and heat, when the resist underlayer composition including the polymer is formed into a resist underlayer, the resist underlayer may experience minimal or reduced stripping by solvents, heat, and/or chemical byproducts during the process of forming a photoresist pattern or generation of by-products, and a thickness loss due to stripping by the solvent used in the overlying photoresist may be reduced or minimized.

In some embodiments, when the chemical linkage or structure "—O—CH$_2$—C(-halogen)-" in the polymer, includes a fluorine group (—F) as the (halogen), improved film density and secondary ion generation of the resist underlayer may be obtained, compared with when other halogen groups are used.

In some embodiments, because an etch rate of the resist underlayer during the dry etching process may be improved by the halogen included in the chemical bond in the form of —O—CH$_2$—C(-halogen)-", the resist underlayer may exhibit improved pattern formality.

In some embodiments, because the polymer has excellent solubility and may thus form a resist underlayer having desired or excellent coating uniformity and strong strip resistance, when the polymer is used as a material for the resist underlayer, a substantially uniform thin film may be formed without deteriorating the thickness distribution or forming pin-holes and voids during the baking process, as well as when there is a step difference in the lower substrate (or film); for example, excellent gap-fill and planarization characteristics may be provided.

The resist underlayer composition according to embodiments may provide excellent or suitable coating uniformity and stability, a high refractive index, and a fast etch rate, such that an EUV (Extreme Ultraviolet) lithography process may be applied thereto. A EUV lithography process utilizes light at a wavelength of about 10 nm to about 20 nm, for example, a very short wavelength of about 13.5 nm to form an ultrafine pattern having a width of less than or equal to about 20 nm.

In some embodiments, the polymer may have a weight average molecular weight (Mw) of about 1,000 g/mol to about 100,000 g/mol. For example, the polymer may have a weight average molecular weight of about 1,000 g/mol to about 50,000 g/mol, or about 1,000 g/mol to about 30,000 g/mol. When the weight average molecular weight is within the above range, the carbon content and solubility of the resist underlayer composition including the polymer may be adjusted and thus optimized.

The solvent is not particularly limited as long as it has sufficient solubility or dispersibility in the polymer, and may be at least one of propylene glycol, propylene glycol diacetate, methoxy propanediol, diethylene glycol, diethylene glycol butylether, tri(ethylene glycol)monomethylether, propylene glycol monomethylether, propylene glycol monomethylether acetate, cyclohexanone, ethyl lactate, gamma-butyrolactone, N,N-dimethyl formamide, N,N-dimethyl acetamide, methylpyrrolidone, methylpyrrolidinone, acetylacetone, or ethyl 3-ethoxypropionate.

The polymer may be included in an amount of about 0.1 wt % to about 50 wt %, about 0.1 wt % to about 30 wt %, or about 0.1 wt % to about 15 wt % based on a total amount of the resist underlayer composition. Within the above ranges, the thickness, surface roughness, and degree of planarization of the resist underlayer may be adjusted.

In some embodiments, the resist underlayer composition may further include at least one other polymer selected from an acrylic resin, an epoxy resin, a novolac resin, a glycoluril resin, and a melamine resin, in addition to the polymers described above, but is not limited thereto.

The resist underlayer composition may further include an additive including a surfactant, a thermal acid generator, a plasticizer, or a combination thereof.

The surfactant may be, for example, an alkylbenzene sulfonate salt, an alkylpyridinium salt, polyethylene glycol, a quaternary ammonium salt, and/or the like, but is not limited thereto.

The thermal acid generator may be an acidic compound (such as p-toluene sulfonic acid, trifluoromethanesulfonic acid, pyridinium p-toluene sulfonic acid, salicylic acid, sulfosalicylic acid, citric acid, benzoic acid, hydroxybenzoic acid, naphthalene carbonic acid, 2,4,4,6-tetrabromocyclohexa-2,5-dienone, benzoin tosylate, 2-nitrobenzyl tosylate, and/or an organic sulfonic acid alkylester), but is not limited thereto.

The additive may be included in an amount of about 0.001 parts by weight to about 40 parts by weight based on 100 parts by weight of the resist underlayer composition. Within the above range, solubility may be improved without changing the optical properties of the resist underlayer composition.

According to another embodiment, a resist underlayer prepared by utilizing the aforementioned resist underlayer composition is provided. The resist underlayer may be formed by coating the aforementioned resist underlayer composition on, for example, a substrate, and then curing the coated composition through a heat treatment process. The resist underlayer may be, for example, an anti-reflection coating.

Hereinafter, a method of forming a pattern using the aforementioned resist underlayer composition is described with reference to FIGS. 1 to 5.

FIGS. 1 to 5 are cross-sectional views illustrating a method of forming a pattern using the resist underlayer composition according to the present disclosure.

Figure 1:
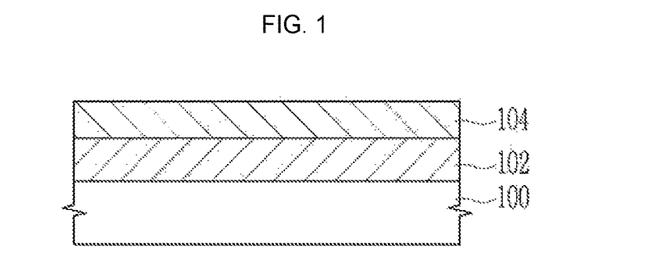
FIGS. 1-5 are cross-sectional views illustrating a method of forming patterns using a resist underlayer composition according to an embodiment.

Referring to FIG. 1, an etching target is prepared. The etching target may be a thin film 102 formed on a semiconductor substrate 100. Hereinafter, the etching target is limited to the thin film 102. An entire surface of the thin film 102 is washed to remove impurities and the like remaining thereon. The thin film 102 may be, for example, a silicon nitride layer, a polysilicon layer, or a silicon oxide layer.

Subsequently, the resist underlayer composition including the polymer having moieties represented by Chemical Formulae 1 and 2 and the solvent is coated on the surface of the cleaned thin film 102 by applying a spin coating method.

Then, the coated composition is dried and baked to form a resist underlayer 104 on the thin film 102. The baking may be performed at about 100° C. to about 500° C., for example, about 100° C. to about 300° C. The resist underlayer composition is described above in more detail.

Figure 2:
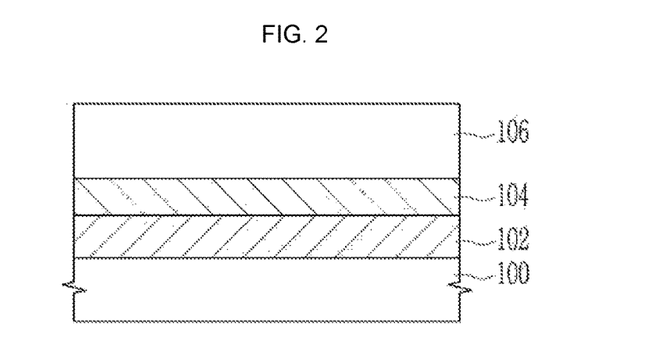

Referring to FIG. 2, a photoresist layer 106 is formed by coating a photoresist on the resist underlayer 104.

Examples of the photoresist include a positive-type photoresist containing a naphthoquinonediazide compound and a novolac resin, a chemically-amplified positive photoresist containing an acid generator capable of dissociating acid through exposure, a compound decomposed under presence of acid and having increased dissolubility in an alkali aqueous solution, an alkali soluble resin, a chemically-amplified positive-type photoresist containing an alkali-soluble resin capable of applying a resin increasing dissolubility in an alkali aqueous solution, and/or the like.

Then, a substrate 100 having the photoresist layer 106 is primarily baked (e.g., baked in a primary or first baking process). The primary baking may be performed at about 90° C. to about 120° C.

Figure 3:
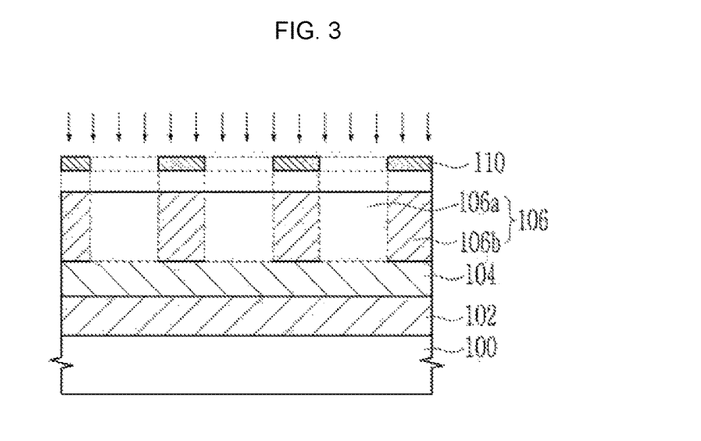

Referring to FIG. 3, the photoresist layer 106 may be selectively exposed.

Exposure of the photoresist layer 106 may be for example performed by positioning an exposure mask 110 having a set or predetermined pattern on a mask stage of an exposure apparatus and aligning the exposure mask 110 on the photoresist layer 106. Subsequently, a set or predetermined region of the photoresist layer 106 formed on the substrate 100 (e.g., a region of the photoresist layer 106 exposed by the exposure mask 110) selectively reacts with light passing the exposure mask by radiating light into the exposure mask 110.

For example, the light used during the exposure may include short wavelength light (such as an activated irradiation i-line having a wavelength of 365 nm, a KrF excimer laser having a wavelength of 248 nm, and/or an ArF excimer laser having a wavelength of 193 nm). In some embodiments, EUV (extreme ultraviolet) light having a wavelength of 13.5 nm may be used.

The photoresist layer of the exposed region 106a is a relatively hydrophilic compared with the photoresist layer 106 of the unexposed region (e.g., 106b). Accordingly, the exposed region 106a and non-exposed region 106b of the photoresist layer 106 may have different solubilities from each other.

Subsequently, the substrate 100 is secondarily baked (e.g., baked in a secondary or second baking process). The secondary baking may be performed at about 90° C. to about 150° C. The exposed region of the photoresist layer may then become easily soluble in a set or predetermined solvent due to the secondary baking.

Figure 4:
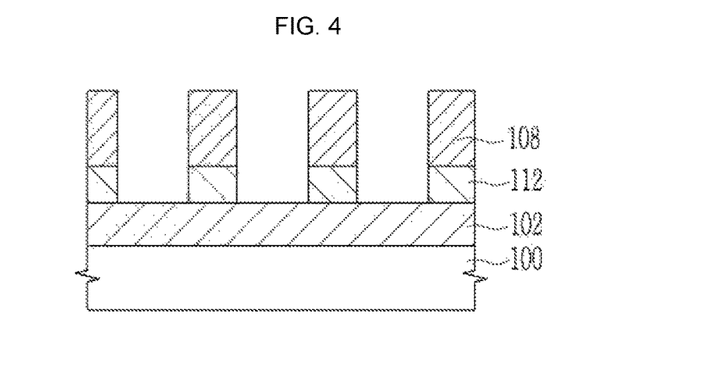

Referring to FIG. 4, the exposed region 106a of the photoresist layer is dissolved and removed by a developing solution to form a photoresist pattern 108. For example, the exposed region 106a of the photoresist layer is dissolved and removed by utilizing a developing solution (such as tetramethyl ammonium hydroxide (TMAH) and/or the like) to finish (provide) the photoresist pattern 108.

Subsequently, the photoresist pattern 108 is used as an etching mask to etch the resist underlayer. Through the etching, an organic layer pattern 112 is formed. The etching may be for example dry etching by using etching gas, and the etching gas may be, for example, $CHF_3$, $CF_4$, $Cl_2$, $O_2$, or a mixed gas thereof. As described above, because the resist underlayer formed by the resist underlayer composition according to the embodiment has a fast etch rate, a smooth etching process may be performed within a short time.

Figure 5:
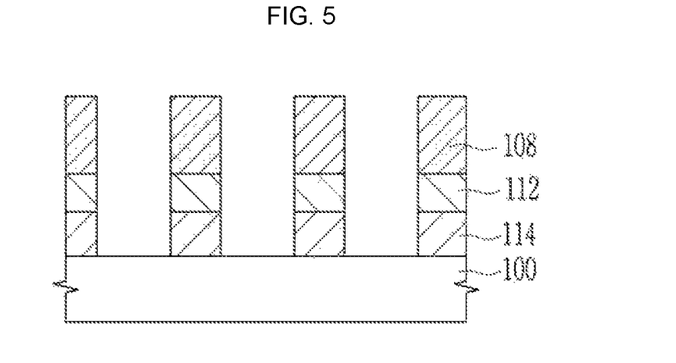

Referring to FIGS. 4 and 5, the photoresist pattern 108 is applied as an etching mask to etch the exposed thin film 102. As a result, the thin film is formed into a thin film pattern 114. In this regard, a thin film pattern formed by an exposure process utilizing a short wavelength light source (such as, for example, an activated irradiation i-line (a wavelength of 365 nm), a KrF excimer laser (a wavelength of 248 nm), an ArF excimer laser (a wavelength of 193 nm), and/or the like) may have a width of tens to hundreds of nm, while a thin film pattern formed by an exposure process utilizing an EUV light source may have a width of less than or equal to about 20 nm.

Hereinafter, the present disclosure is described in more detail through Examples regarding synthesis of the polymer and preparation of a resist underlayer composition including the same. However, the present disclosure is not limited to the following embodiments.

SYNTHESIS EXAMPLES

Synthesis Example 1

5.0 g of 1-[(hydroxyethyl]-3,5-bis[3-[(2-hydroxyethyl) thio]propyl]-1,3,5-triazine-2,4,6-trione, 5.0 g of 2-propenoic acid, 1,1'-(2,2,3,3,4,4,5,5-octafluoro-1,6-hexanediyl)ester, 0.22 g of AIBN, and 16 g of N,N-dimethyl formamide (DMF) were put in a 100 mL round flask equipped with a condenser, and then heated with magnetic stirring to perform a polymerization reaction at 80° C. After performing the reaction for 10 hours, the resultant was cooled down to room temperature (23° C.) and three times purified using toluene and hexane to obtain a polymer including a structural unit represented by Chemical Formula 3 (a molecular weight (Mw)=4,000 g/mol).

Synthesis Example 2

5.0 g of 1,3-diallyl-5-(2-hydroxyethyl)-1,3,5-triazinane-2,4,6-trione, 5.0 g of 2-propenoic acid, 1,1'-(2,2,3,3-tetrafluoro-1,4-butanediyl)ester, 0.22 g of AIBN, and 16 g of N,N-dimethyl formamide (DMF) were put in a 100 mL round flask equipped with a condenser, and then heated with magnetic stirring to perform a polymerization reaction at 80° C. After performing the reaction for 10 hours, the resultant was cooled down to room temperature (23° C.) and three times purified using toluene and hexane to obtain a polymer including a structural unit represented by Chemical Formula 4 (a molecular weight (Mw)=3,800 g/mol).

Synthesis Example 3

5.0 g of 1,3-diallyl-5-(2-hydroxyethyl)-1,3,5-triazinane-2,4,6-trione, 5.0 g of 2-propenoic acid, 1,1'-(2,2,3,3,4,4-hexafluoro-1,5-pentanediyl)ester, 0.22 g of AIBN, and 16 g of N,N-dimethyl formamide (DMF) were put in a 100 mL round flask equipped with a condenser, and then heated with magnetic stirring to perform a polymerization reaction at 80° C. After performing the reaction for 10 hours, the resultant was cooled down to room temperature (23° C.) and three times purified using toluene and hexane to obtain a polymer including a structural unit represented by Chemical Formula 5 (a molecular weight (Mw)=4,100 g/mol).

Synthesis Example 4

2 g of 1,3-diallyl-5-(2-hydroxyethyl)-1,3,5-triazinane-2,4,6-trione and 3.7 g of 1,6-dihydroxy-2,2,3,3,4,4,5,5-octafluorohexane were dissolved in 50 g of propylene glycol monomethylether. Subsequently, 3.5 g of iodine was slowly added to the reaction solution at 0° C. and then, heated up to room temperature (23° C.). When the reaction starting materials were completely consumed, the reaction solution was quenched with 10% aqueous $Na_2S_2O_5$ (500 mL) to obtain a polymer including a structural unit represented by Chemical Formula 6 (a molecular weight (Mw)=5,300 g/mol).

Comparison Synthesis Example 1

23.31 g of 1,3-bis(isocyanatomethyl)cyclohexane, 62.7 g of trihydroxyethylisocyanurate, 0.67 g of DABCO, and 201 g of tetrahydrofuran (THF) were put in a 500 mL 2-necked round flask, and a condenser was connected thereto. The obtained mixture was heated up to 75° C. and reacted for 5 hours, and the corresponding reaction solution was cooled down to room temperature (23° C.). Subsequently, the reaction solution was moved to a 1 L wide-mouthed bottle, three times washed with hexane, and subsequently, washed with purified water. The obtained resin in a gum state was completely dissolved in 80 g of THF and then, slowly added in a dropwise fashion to 800 g of toluene, while the solution was stirred. The solvent was decanted and the remaining solvent was removed using a vacuum pump to obtain a polymer including a structural unit represented by Chemical Formula 7 (Mw=5,200 g/mol).

Chemical Formula 7

In Chemical Formula 7, * is a linking point.

Comparison Synthesis Example 2

9.3 g of tris(2-hydroxyethyl)isocyanurate, 10.0 g of dimethyl 3,3'-(5-allyl-isocyanurate-1,3-diyl)dipropionate, 0.2 g of p-toluene sulfonic acid, and 45 g of anisole were put in a 100 mL round flask equipped with a condenser and then heated with magnetic stirring until a polymerization reaction was initiated. After 1 hour, when the internal temperature reached 150° C. or higher, 20 g of reaction by-products and solvents were removed through decompression (e.g., under vacuum) to concentrate and promote the reaction. After performing the reaction for 15 minutes, the resultant was cooled down to room temperature (23° C.) and 5 times purified using isopropyl alcohol and hexane to remove small molecules and a catalyst and finally obtain a polymer including a structural unit represented by Chemical Formula 8 (a molecular weight (Mw)=8,000 g/mol).

Chemical Formula 8

In Chemical Formula 8, * is a linking point.

Preparation of Resist Underlayer Composition

Examples 1 to 5 and Comparative Examples 1 to 2

1 g of each polymer according to Synthesis Examples 1 to 5 and Comparative Synthesis Examples 1 to 2, along with 0.15 g of PD1174 (a hardener, TCI) and 0.01 g of pyridinium para-toluene sulfonate (PPTS), was dissolved in 98.84 g of a mixed solvent of propylene glycol monomethylether and ethyl lactate (a volume ratio=1:1) and then, stirred for 6 hours to prepare a series of resist underlayer compositions.

Coating Uniformity Evaluation 2 mL aliquots of the resist underlayer compositions according to Examples 1 to 5 and Comparative Examples 1 to 2 were each respectively cast on an 8-inch wafer and spin-coated at 1,500 rpm for 20 seconds using an Auto Track (ACT-8, TEL (Tokyo Electron Ltd.) and then, cured at 210° C. for 90 seconds to respectively form 300 nm-thick resist underlayers. Subsequently, film thicknesses at 51 points on the horizontal axis of each film were measured to compare coating uniformity, and the results are shown in Table 1.

In Table 1, the smaller the coating uniformity (%), the better or more excellent the coating uniformity.

TABLE 1

|  | Coating uniformity (%) |
| --- | --- |
| Example 1 | 1.1 |
| Example 2 | 1.2 |
| Example 3 | 1.1 |
| Example 4 | 1.0 |
| Comparative Example 1 | 1.5 |
| Comparative Example 2 | 1.8 |

Referring to Table 1, the films formed of the resist underlayer compositions according to Examples 1 to 4 exhibited (improved) excellent coating uniformity compared with the films formed of the resist underlayer compositions according to Comparative Examples 1 to 2.

Film Density Evaluation

The resist underlayer compositions according to Examples 1 to 4 and Comparative Examples 1 to 2 were respectively spin-coated on a silicon substrate, and then heat-treated on a hot plate at 205° C. for 1 minute to form about 30 nm-thick resist underlayers.

Subsequently, the densities of each of the resist underlayers were measured, and the results are shown in Table 2. The densities of each of the resist underlayers were measured using an X-Ray diffractometer (Model: X'Pert PRO MPD, Malvern Panalytical Ltd.).

TABLE 2

|  | Film density (g/cm$^3$) |
| --- | --- |
| Example 1 | 1.47 |
| Example 2 | 1.45 |
| Example 3 | 1.44 |
| Example 4 | 1.43 |
| Comparative Example 1 | 1.33 |
| Comparative Example 2 | 1.34 |

Referring to Table 2, each of the films formed of the resist underlayer compositions according to Examples 1 to 4 exhibited a high density, compared with the films formed of the resist underlayer compositions according to Comparative Examples 1 to 2. For example, when the resist underlayer compositions according to the Examples were used, the Examples provided a film with a denser structure than the Comparative Examples.

Evaluation of Exposure Characteristics

Each of the compositions of Examples 1 to 4 and Comparative Examples 1 to 2 were coated in a spin-on coating method, and then heat-treated on a hot plate at 205° C. for 1 minute to form about 10 nm-thick resist underlayers.

Subsequently, on each of the photoresist underlayers, a photoresist solution was coated in the spin-on coating method, and then heat-treated on a hot plate at 110° C. for 1 minute to form photoresist layers. The photoresist layers were each exposed to an acceleration voltage of 100 keV utilizing an e-beam exposer (Elionix Inc.) and then, heat-treated at 110° C. for 60 seconds. Subsequently, the photoresist layers were developed with an aqueous solution of 2.38 mass % (wt %) tetramethylammonium hydroxide (TMAH) at 23° C., and then rinsed with pure water for 15 seconds to form a photoresist pattern of line and space (L/S).

Then, an optimal exposure dose of the photoresist pattern was evaluated, and the results are shown in Table 3.

Herein, the optimal exposure dose (Eop) is an exposure dose that resolves a 40 nm line and space (L/S) photoresist pattern at 1:1 ($\mu$C/cm$^2$), and in the optimal exposure dose, a minimum linewidth of the line and space is referred to as resolution. The resolution was evaluated by measuring a limit resolution (nm) with a scanning electron microscope (SEM) S-9260 (Hitachi Ltd.).

TABLE 3

|  | Eop ($\mu$C/cm$^2$) |
| --- | --- |
| Example 1 | 270 |
| Example 2 | 260 |
| Example 3 | 270 |
| Example 4 | 270 |
| Comparative Example 1 | 330 |
| Comparative Example 2 | 330 |

Referring to Table 3, the resist underlayers formed of the compositions according to the Examples each exhibited a better or excellent optimal exposure dose of a photoresist pattern, compared with the resist under layer formed of the compositions according to the Comparative Examples. In other words, the resist underlayer compositions according to the examples turned out to form a photoresist pattern with improved sensitivity, compared with the resist underlayer compositions according to the Comparative Examples.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Hereinbefore, embodiments of the present disclosure have been described and illustrated, however, it will be apparent to a person with ordinary skill in the art that the present disclosure is not limited to the embodiment as described, and may be variously modified and/or transformed without departing from the spirit and scope of the present disclosure. Accordingly, the modified or transformed embodiments as such are included within the technical ideas and aspects of the present disclosure, and the modified embodiments are within the scope of the appended claims and equivalents thereof.

| Description of Some of the Symbols | |
| --- | --- |
| 100: substrate | 102: thin film |
| 104: resist underlayer | 106: photoresist layer |

| Description of Some of the Symbols | |
|---|---|
| 108: photoresist pattern | 110: mask |
| 112: organic layer pattern | 114: thin film pattern |

What is claimed is:

1. A resist underlayer composition comprising:
a polymer consisting of a structural unit represented by Chemical Formula 4 and/or Formula 5; and
a solvent:

Chemical Formula 4

Chemical Formula 5 and
wherein, in Chemical Formulae 4 and 5, * is a linking point.

2. The resist underlayer composition of claim 1, wherein the polymer has a weight average molecular weight (Mw) of about 1,000 g/mol to about 100,000 g/mol.

3. The resist underlayer composition of claim 1, wherein the polymer is comprised in an amount of about 0.1 wt % to about 50 wt % based on a total amount of the resist underlayer composition.

4. The resist underlayer composition of claim 1, wherein the resist underlayer composition further comprises at least one polymer selected from an acrylic resin, an epoxy resin, a novolac resin, a glycoluril resin, and a melamine resin.

5. The resist underlayer composition of claim 1, further comprising an additive comprising a surfactant, a thermal acid generator, a plasticizer, or a combination thereof.

6. A method of forming patterns, the method comprising:
forming an etching target layer,
coating the resist underlayer composition of claim 1 on the etching target layer to form a resist underlayer,
forming a photoresist pattern on the resist underlayer, and
sequentially etching the resist underlayer and the etching target layer utilizing the photoresist pattern as an etching mask.

7. The method of claim 6, wherein the forming of the photoresist pattern comprises:
forming a photoresist layer on the resist underlayer;
exposing the photoresist layer; and
developing the photoresist layer.

8. The method of claim 6, wherein the forming of the resist underlayer further comprises heat treating at about 100° C. to about 500° C. after coating the resist underlayer composition.

* * * * *